(12) United States Patent
Lei

(10) Patent No.: US 8,043,210 B2
(45) Date of Patent: Oct. 25, 2011

(54) ENDOSCOPE TUBE WITH IMAGE INVERSION SYSTEM

(75) Inventor: Fang Lei, Durchhausen (DE)

(73) Assignee: Karl Storz GmbH & Co. KG (DE)

( * ) Notice: Subject to any disclaimer, the term of this patent is extended or adjusted under 35 U.S.C. 154(b) by 1221 days.

(21) Appl. No.: 11/687,073

(22) Filed: Mar. 16, 2007

(65) Prior Publication Data

US 2007/0219414 A1 Sep. 20, 2007

(30) Foreign Application Priority Data

Mar. 16, 2006 (DE) .......................... 10 2006 012 563

(51) Int. Cl.
*A61B 1/00* (2006.01)
*G02B 23/24* (2006.01)
(52) U.S. Cl. ........................................ 600/138; 359/435
(58) Field of Classification Search .................. 600/138, 600/161–162, 173; 359/434–435
See application file for complete search history.

(56) References Cited

U.S. PATENT DOCUMENTS

| | | | | |
|---|---|---|---|---|
| 4,148,551 A | * | 4/1979 | MacAnally | 359/435 |
| 4,608,966 A | * | 9/1986 | Storz | 600/161 |
| 5,020,893 A | * | 6/1991 | Karst et al. | 359/435 |
| 5,206,759 A | * | 4/1993 | Ono et al. | 359/434 |
| 5,805,345 A | | 9/1998 | Nagaoka | 359/654 |
| 5,892,625 A | * | 4/1999 | Heimer | 359/665 |
| 5,999,344 A | * | 12/1999 | Wulfsberg et al. | 359/819 |
| 6,398,723 B1 | * | 6/2002 | Kehr et al. | 600/160 |
| 6,471,640 B1 | * | 10/2002 | Frische et al. | 600/138 |
| 6,955,644 B2 | * | 10/2005 | Forkey et al. | 600/133 |
| 7,586,679 B2 | * | 9/2009 | Lei | 359/434 |
| 7,699,773 B2 | * | 4/2010 | Forkey et al. | 600/172 |
| 2001/0039371 A1 | * | 11/2001 | Forster | 600/176 |
| 2003/0179448 A1 | * | 9/2003 | Ramsbottom | 359/435 |
| 2005/0240079 A1 | * | 10/2005 | Baholzer | 600/160 |

FOREIGN PATENT DOCUMENTS

| | | |
|---|---|---|
| DE | 38 39 364 A1 | 5/1990 |
| DE | 197 42 454 A1 | 4/1999 |
| DE | 199 12 656 A1 | 11/2000 |
| DE | 10 2004 019 909 A1 | 12/2004 |

\* cited by examiner

*Primary Examiner* — Philip Smith
(74) *Attorney, Agent, or Firm* — St. Onge Steward Johnston & Reens LLC

(57) ABSTRACT

An endoscope tube having at least one image inversion system consisting of two rod lenses, in which the first rod ends, pointing to an intermediate image plane, have a marginal cylinder, which is mounted in the endoscope tube, in which the second rod ends, which lie symmetrical to an aperture plane, have a diameter that is smaller than the inner diameter of the endoscope tube, so that the end surfaces associated with the first rod lenses are convex in configuration, the end surfaces associated with the second rod ends can be cemented together with a lens element, and a distance holder that defines the aperture area is inserted between the two rod lenses, is characterized in that the rod diameter in each case continually decreases from the marginal cylinder toward the second rod end.

12 Claims, 3 Drawing Sheets

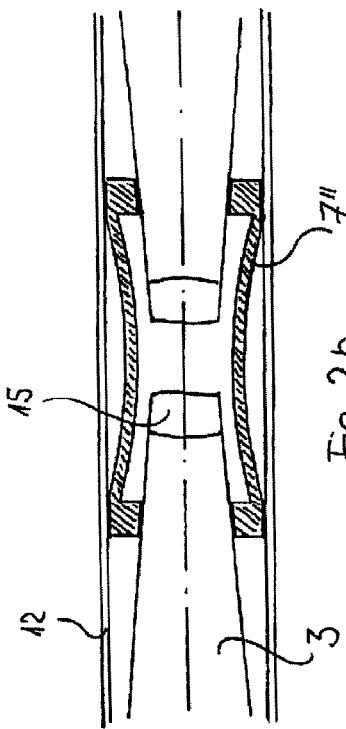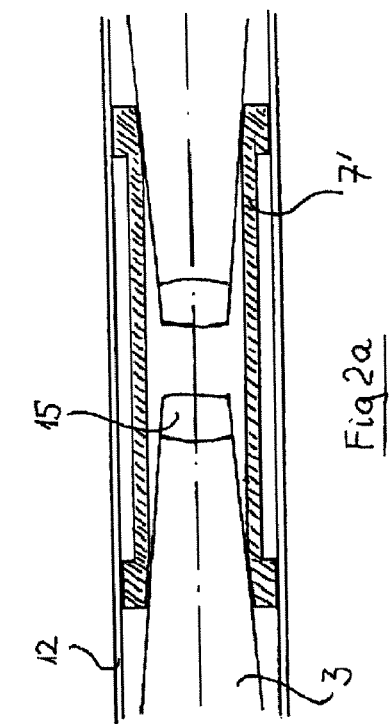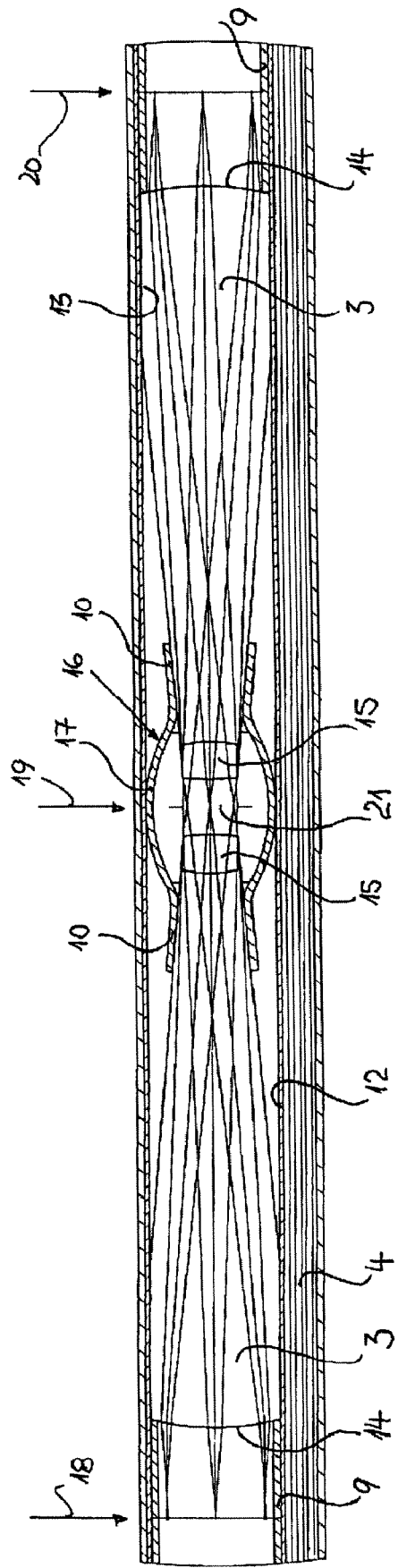

ENDOSCOPE TUBE WITH IMAGE INVERSION SYSTEM

CROSS-REFERENCE TO RELATED APPLICATIONS

The present application claims priority of German patent application No. 10 2006 012 563.0 filed on Mar. 16, 2006, the content of which is incorporated herein by reference.

FIELD OF THE INVENTION

The invention relates to an endoscope tube having at least one image inversion system that consists of two rod lenses and corresponding to the characteristics in the generic terms of claim 1.

BACKGROUND OF THE INVENTION

A system of this type is disclosed in DE 38 39 364 C2. Each of the rod lenses has on its first rod end a marginal cylinder whose diameter is adjusted to the inner diameter of the endoscope tube. The marginal cylinder has a length of about two-thirds the total length of the rod lens and serves to store the rod lens in the endoscope tube. The second rod end likewise includes a marginal cylinder whose diameter, however, is smaller than the inner diameter of the endoscope tube. The sudden transition from a thicker to a thinner rod lens part increases the danger of breakage at this spot during processing and during insertion of the endoscope tube.

The end surface of the thicker marginal cylinder is convex. At the end surface of the thinner marginal cylinder, a corrective lens is cemented. The convex end surfaces point to an intermediate image plane. The corrective lenses enclose a lens aperture.

It is known in the prior art that rod lenses in the area of cemented surfaces, when the endoscope tube is subject to bending, are exposed to increased danger of breakage. Reducing the rod diameter in this area is intended to avoid any impact from the bending in the cemented area. For configuring the aperture area, however, it is necessary that a distance holder should be inserted between the two rod lenses. This distance holder takes the form of a small tube, which on the one hand is contiguous to the endoscope tube and on the other hand is supported on the corrective lenses in the axial direction. During the exertion of bending pressure of the endoscope tube, it therefore is unavoidable that radially varying axial pressures are exerted on the cemented corrective lenses by the small distancing tube. These pressures can lead to damaging of the cemented surface or of the end surface and thus to a decline in the optical imaging quality.

Bending pressure on the endoscope tube also acts directly on the relatively long, thicker marginal cylinder and can result in breaking of the rod lens.

It is therefore the object of the invention to configure the rod lenses in such a way that their fragility when positioned in an endoscope tube is minimized and to provide a distance holder adapted thereto.

SUMMARY OF THE INVENTION

In an endoscope tube with image reversal system of the aforementioned type, this object is fulfilled according to the invention by means of the decisive characteristics of claim 1 and by means of a distance holder having the characteristics of claim 11. Advantageous configurations and refinements can be seen from the characteristics of the subsidiary claims.

The greater distance to the endoscope tube, achieved through the tapering of the rod ends at this spot, can be used for configuring the distance holder as an elastic support body for the tapered rod ends.

The rod end of the rod lenses, which is continuously tapering and in particular has a cone shape, allows this rod end to be stored in a fixed axial direction over its housing surface without coming in contact with the endoscope tube. When the rod end has a conical shape, the mounting position can be adapted in especially simple manner to the mantle surface. The ratio of the diameters of the rod ends to the rod length results in relatively large conical angles, which support the fixing of the mounting in the axial direction. The relatively short, thicker marginal cylinder offers little gripping surface for bending forces on the endoscope tube.

For mounting the conical-shaped rod ends, it is especially appropriate to have a distance holder that contains on both sides at least a short funnel-shaped recess. The funnel is open toward the aperture space. On the basis of the length of the distance holder as well as the angle of aperture and diameter of the aperture of the funnel, the positioning of the two rod ends can be adjusted in such a way that the particular cement surfaces or end surfaces of the rod ends lie free in the aperture space and the distance of the lens elements to the aperture plane corresponds to a predetermined value.

The distance holder is preferably manufactured of an elastic material that can compensate for agitation caused by blows and even stronger bendings on the endoscope tube. In addition the distance holder can be configured in such a way that it is supported on the endoscope tube radially by springs. The distance holder can be executed in a single piece as an injection-molded part. It is also possible, however, for the distance holder to consist of several segments divided up in an axial direction.

By configuring the distance holder as elastic in the radial direction and rigid in the axial direction, with recesses positioned around the outer margins of the beam pass-through aperture for the tapered rod ends, it is also possible to have a protective front-end recess for the rod ends.

An embodiment for an endoscope tube according to the invention, having an image inversion system, is schematically depicted in the illustration and is described hereafter with reference to the illustrations.

BRIEF DESCRIPTION OF THE DRAWINGS

FIG. 2a, b shows various versions of a distance holder.

FIG. 3 shows the cross-section of an additional embodiment.

DETAILED DESCRIPTION OF THE INVENTION

Figure 1:
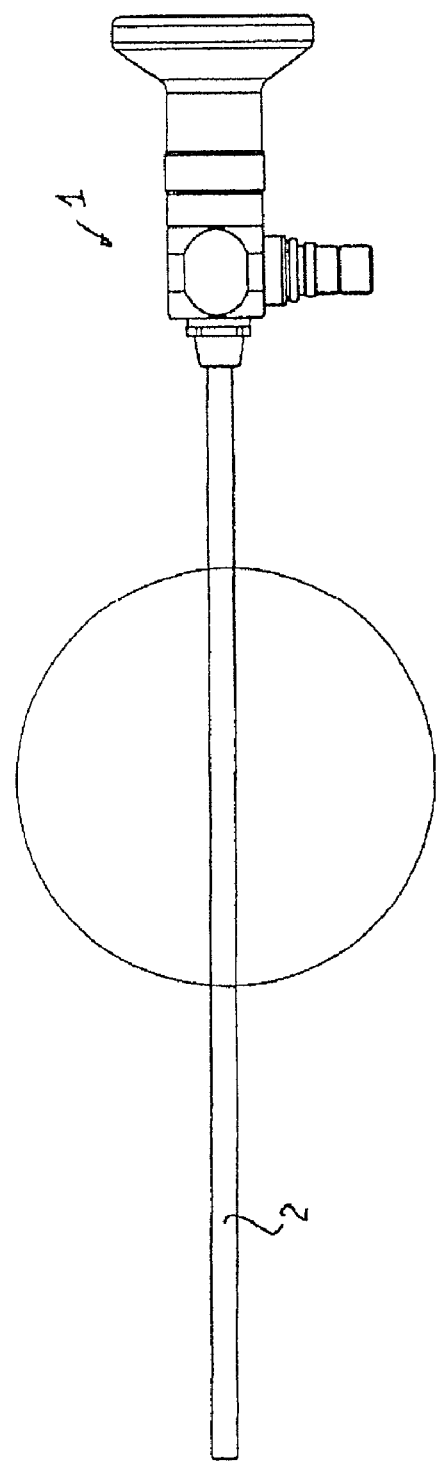
FIG. 1 shows a familiar endoscope from the prior art having a rigid insertion art.

In FIG. 1 is seen a familiar endoscope 1 from prior art, with a rigid insertion part 2. A section cut out of the insertion part, marked with a circle, is schematically depicted in cross-section in FIG. 2. The insertion part 2 contains in general separate tubes for installing the rod lenses 3 and a light fiber bundle 4, as is shown more precisely in FIG. 3.

Figure 2:
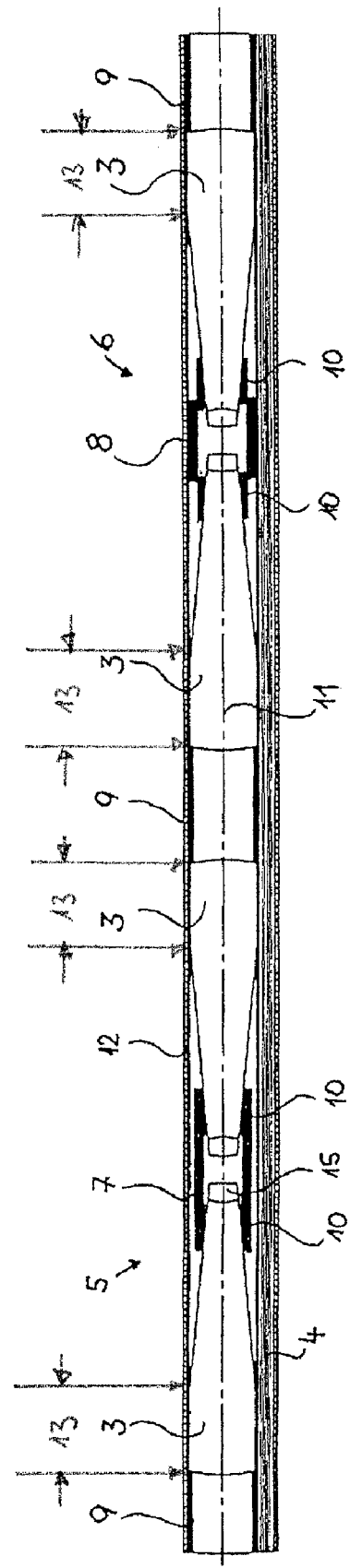
FIG. 2 shows a section of the insertion part in cross-section.

FIG. 2 shows two image inversion systems 5, 6. Each of the image inversion systems 5, 6 consists of two conical rod lenses 3, which are held together and aligned to one another by a distance holder 7, 8 in the area of the thinner rod ends. If these two rod lenses lying opposite to one another on the thinner rod ends are observed, they can each be seen as half of a bone-shaped rod lens, which are held together by the distance holders. The two image inversion systems 5,6 are kept at a distance to one another by a small distance tube 9.

A first distance holder 7 contains in the axial direction a funnel-shaped recess 10 on each side, which surrounds the conical thinner rod ends of the rod lens 3. The distance holder 7 is suspended and connected with the rod lenses 3. As FIG. 2a shows, the distance holder 7' in the area of the funnel-shaped recess 10 can also be equipped with a bulged border for supporting it on the inner wall of the tube. Instead of a cylindrical distancing part, it can also be configured as a tapered rotation body 7", which has an improved rigidity against bending forces.

A second distance holder 8 also contains a funnel-shaped recess 10 on each side. In the center area it supports itself, however, on the inner tube wall. In this manner, in addition, a better load distribution is achieved for the rod ends and better centering of the optical axes 11 of the rod lenses 3. The support can be configured as elastic.

In FIG. 3 is shown an enlarged detail from the insertion part 2 with an image inversion system 6 shown in detail. In a separate endoscope tube 12, the two rod lenses 3 are mounted with their marginal cylinders. The rod lenses 3 on this thicker end have convex front surfaces 14. Lens elements 15 are cemented on the thinner ends of the rod lenses 3.

The additional distance holder 16 has a center part, which is configured as a bulgy rotation body 17. Each side has funnel-shaped recesses shaped on it, whose angle of aperture is adjusted to the conical tapering of the rod lenses 3. The rotation-shaped bulgy center part of the distance holder 16 is supported with springs on the endoscope tube 12. The inner diameter of aperture of the funnel-shaped part is large enough so that the cemented surface for the lens element 15, when the rod lens 3 is completely inserted, lies outside the recess 10. The distance holder 16 can be made of metal or plastic and can be cemented with the conical parts of the rod lenses 3.

The geometric dimensions of the rod lenses 3 are selected in such a way that in the area of the funnel-shaped recess 10, there is a conical shape on the thinner end of the rod lens 3 that is sufficient for a safe axial fixing. The length of the marginal cylinder 13 should be smaller than or equal to one-third of the total length of the rod lens 3, so that enough space is available for the folding of the endoscope tube. The length of the marginal cylinder 13, however, should be larger than half the diameter of the rod lens 3 at this spot, so that enough surface is configured to support the rod lens 3. If the diameter of the marginal cylinder 13 under these conditions is equal to one-fifth of the rod length and the diameter of the end surface of the other rod end is equal to about one-tenth of the rod length, the result is a conical angle, which ensures a secure position in the funnel-shaped recess 10 even without additional cementing.

From the course of the imaging ray cluster, also seen in the illustration, from a first intermediate image plane 18 by way of the aperture plane to a second intermediate image plane 20, it can be seen that the system possesses a numeric aperture that can be compared to conventional rod lens arrangements. In the short rod lengths, determined by their construction, this aperture is achieved by a corresponding contraction of the effective diameter in the aperture area. This contraction, on the other hand, creates the space for the insertion of the distance holder or supporting body, according to the invention.

Figure 4:
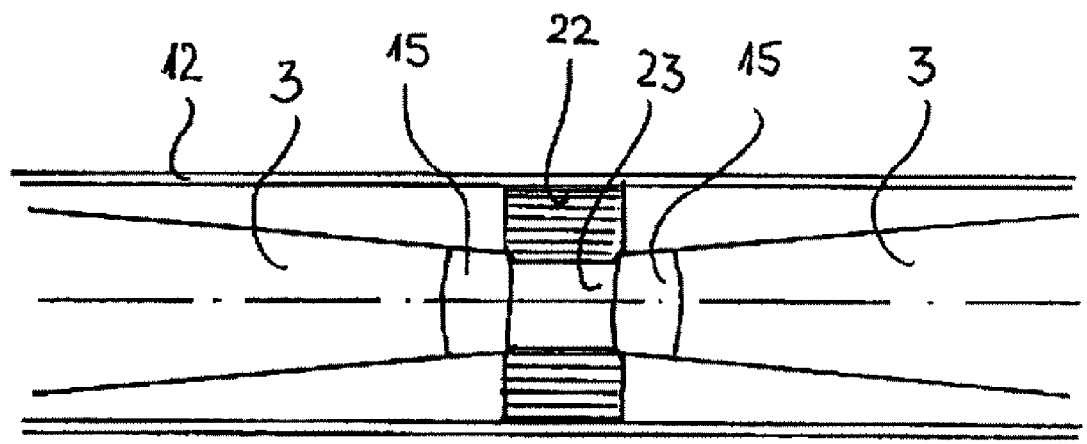
FIG. 4 shows a disk-shaped distance holder with front-end projection.

FIG. 4 shows a disc-shaped distance holder with a ray pass-through aperture 23 for a front-side insertion of the contracted rod ends. The horizontal strips in the cross-section of the disc-shaped body 22 are meant to indicate the rigidity in the axial direction, and the distance between the strips to indicate the elasticity in the radial direction. During bending pressure on the endoscope tube, nearly no shearing forces act on the cemented lens elements 15 on the rod ends, because these ends are diverted over the relatively thick elastic disc ring. If the disc body is made of plastic, there arise no frictional forces that could lead to damaging of the surface. The projection on the distance holder 22 occurs only in a short marginal area of the beam pass-through aperture 23. This shape for a distance holder 22 is especially advantageous in contracted rod ends without cemented-on lens elements, as is the case for instance in the aforementioned joining together of two half bone-shaped rod lenses.

What is claimed is:

1. An endoscope tube having:
   at least one image inversion system consisting of two rod lenses, each having first and second rod ends;
   in which the first rod ends point to an intermediate image plane and an edge cylinder which is mounted in the endoscope tube;
   in which the second rod ends lie symmetrically to an aperture plane;
   wherein the end surfaces associated with the first rod ends are configured as convex and the end surfaces associated with the second rod ends can be cemented with a lens element; and
   wherein a distance holder that bridges the aperture plane is inserted to hold the second rod ends;
   characterized in that the diameter of each rod lens continually decreases from the inner edge of the edge cylinder to the second rod end.

2. The endoscope tube of claim 1, wherein the rod lenses between the edge cylinder and the second rod end are configured in a conical shape.

3. The endoscope tube of claim 1, wherein the diameter of the edge cylinder is equal to about one-fifth of the rod length and the diameter of the end surface of the second rod ends to about one-tenth the rod length.

4. The endoscope tube of claim 1, wherein the length of the edge cylinder in each case is less than or equal to one-third of the total length of the rod lens and is greater than half of the diameter of the edge cylinder.

5. The endoscope tube according to of claim 1, wherein the distance holder is configured with a recess on each side in the axial direction, open to the aperture area, for the second rod lens.

6. The endoscope tube of claim 5, wherein the recess open in the axial direction has a funnel shape.

7. The endoscope tube of claim 5, wherein the endoscope also has an aperture angle and aperture diameter of the recess, wherein the length of the distance holder, the aperture angle, and the aperture diameter of the recess are adjusted to the shape of the second rod ends in such a way that in their projection the cemented surface of a lens element lies free in the aperture area and a predetermined distance occurs from the lens element to the aperture plane.

8. The endoscope tube of claim 5, wherein the distance holder is formed as a disc-shaped body that is elastic in the radial direction and rigid in the axial direction, and which has a aperture passing through in the axial direction for an imaging beam parcel, so that the outer margins of the aperture are configured so that they widen toward the axially directed contracted rod ends.

9. The endoscope tube of claim 8, wherein the edges is configured so that it widens like a funnel toward the recess of convex shaped rod lens margins.

10. The endoscope tube of claim 5, wherein the distance holder is made of an elastic material.

11. The endoscope tube of claim 5, wherein the distance holder is radially contiguous and springed to the endoscope tube.

12. The endoscope tube of claim 5, wherein the distance holder is made as a single die-cast mold piece.

* * * * *